United States Patent [19]

Sugawara

[11] Patent Number: 5,293,217

[45] Date of Patent: Mar. 8, 1994

[54] BONDING WIRE INSPECTION APPARATUS

[75] Inventor: Kenji Sugawara, Tokyo, Japan

[73] Assignee: Kabushiki Kaisha Shinkawa, Tokyo, Japan

[21] Appl. No.: 988,731

[22] Filed: Dec. 10, 1992

[30] Foreign Application Priority Data

Dec. 10, 1991 [JP] Japan .................................. 3-349754

[51] Int. Cl.$^5$ .............................................. G01B 11/00
[52] U.S. Cl. ..................................... 356/372; 356/375; 250/561
[58] Field of Search ............... 356/372, 375, 376, 394, 356/237, 384, 444; 250/561, 562, 563, 572; 358/106, 107

[56] References Cited

U.S. PATENT DOCUMENTS

| 2,731,878 | 1/1956 | Sherwin | 356/444 |
| 4,373,817 | 2/1983 | Coates | 356/384 |
| 4,872,052 | 10/1989 | Liudzius et al. | 356/394 |
| 4,874,956 | 10/1989 | Kato et al. | 250/561 |
| 5,030,008 | 7/1991 | Scott et al. | 356/394 |
| 5,138,180 | 8/1992 | Yamanaka | 356/394 |

FOREIGN PATENT DOCUMENTS 3-76137  4/1991  Japan .

Primary Examiner—F. L. Evans
Attorney, Agent, or Firm—Koda and Androlia

[57] ABSTRACT

An apparatus for inspecting, for example, balls and crescents of wires bonded between a semiconductor chip and a lead frame including an optical system installed above an object of inspection, a vertical illuminator that illuminates the object of inspection, a CCD camera which has a photoelectric converter element provided at an imaging level of the optical system, and X, Y and Z tables which move the CCD camera in the X, Y and Z directions. Since only the photoelectric converter element of the CCD camera is movable in the X, Y and Z directions when focusing is made into the object of inspection, the size of the X, Y and Z tables can be small, and in addition, since the optical system and vertical illuminator are not movable, dirt is prevented from falling onto the object of inspection.

2 Claims, 3 Drawing Sheets

BONDING WIRE INSPECTION APPARATUS

BACKGROUND OF THE INVENTION

1. Field of the Invention

The present invention relates to a bonding wire inspection apparatus that automatically inspects the condition of wires bonded between the pads of a semiconductor chip and the leads of a lead frame.

2. Prior Art

FIGS. 6 through 9 show a sample 6 that is an example to be inspected. The sample 6 includes wires 5 that are bonded between the pads 2 of a semiconductor chip 1 and the leads 4 of a lead frame 3. In these Figures, reference numeral 7 refers to squeezed out paste that is used for bonding the semiconductor chip 1 to the lead frame 3. FIG. 5 shows one of the conventional inspection apparatuses.

In this inspection apparatus, a vertical illumination means 11 is located above the sample 6, which is placed on an inspection stand 10. The vertical illumination means 11 is installed at the bottom of an optical means 12, and a CCD camera 13, that consists of a CCD (photoelectric converter element) and a driving source therefor, is mounted on the top of the optical means 12. The CCD outputs an image signal of the image of the sample 6 taken in by the optical means 12. The image signal from the CCD camera 13 is processed by an image-processing arithmetic unit 14. Thus, the shape of the wire 5 is recognized, and the bonded position of the wire 5 is also observed.

The optical means 12, that includes the vertical illumination means 11 and the CCD camera 13, is provided on an X-Y table 15. Inside the vertical illumination means 11, a half-mirror 16 is installed so that the half-mirror 16 is positioned straight beneath the CCD camera 13. Also inside the vertical illumination means 11 are a condensing lens 17 and a light bulb 18 that are installed on one side of the half-mirror 16.

The bonding wire inspection apparatus of this type is described in, for example, Japanese Patent Application Laid-Open (Kokai) No. 3-76137.

In the apparatus shown in FIG. 5, when the vertical illumination means 11 is switched on, the light from the light bulb 18 passes through the condensing lens 17, is reflected by the half-mirror 16, and then vertically directed onto the sample 6. Then, the X-Y table 15 is moved so that the CCD camera 13 is positioned above the object of inspection or the sample 6 that is on the inspection stand 10, and the image signal (that represents microscopic parts of the object of inspection, such as the ball and crescent at both ends of a bonded wire) obtained by the CCD camera 13 is subjected to noise removal, edge enhancement in the inspection area and enlargement or reduction of the image, etc. by means of the image-processing arithmetic unit 14, thus enhancing (restoring) the image of the microscopic parts of the object of inspection so that the image is easier to see. Afterward, the inspection and measurement operations are performed.

When the microscopic parts of the object of inspection are thus optically imaged, the magnification of the optical means 12 is set at a high value. For example, the magnification is set to be 2 to 3 times larger when a ⅔ inch CCD camera is used.

In recent years, semiconductor chips are increased in size, and the dimensions of the area in which the wire bonding is performed are now as large as 30 mm square or thereabouts. Since the microscopic portions, that are to be inspected, are located in such a broad range as 30 mm square area, it is necessary in the prior art to move the vertical illumination means 11 and the optical system 12, which are heavy in weight, great distance. As a result, the size of the X-Y table needs to be large, which makes rapid movement of the illumination means difficult and increases the cost of the inspection apparatus.

In addition, since the vertical illumination means 11 and the optical system 12 which are located above the sample 6 are moved, dirt, etc. would fall onto the sample 6 as the vertical illumination means 11 and the optical system 12 move. In other words, in semiconductor devices which are extremely averse to contamination by dirt, etc., those parts that move above the sample tends to cause various problems and therefore should be avoided, even in the process in which the sample is under inspection.

SUMMARY OF THE INVENTION

Accordingly, the object of the present invention is to provide a bonding wire inspection apparatus that can increase the speed of inspection and reduce the cost of the apparatus by using parts that are more compact than in the prior art apparatuses.

Another object of the present invention is to provide a bonding wire inspection apparatus that can eliminate the chances that dirt, etc. having a deleterious effect falls on the sample.

The first means of the present invention to achieve the object is characterized in that the inspection apparatus is comprised of an optical system installed above the object of inspection, an illumination means that illuminates the object of inspection, a photoelectric converter element installed at the imaging level of the optical system, and an X-Y table that moves only the photoelectric converter element in the X and Y directions.

The second means of the present invention to achieve the object is characterized in that the inspection apparatus is comprised of an optical system installed above the object to be inspected, an illumination means that illuminates the object of inspection, a photoelectric converter element installed at the imaging level of the optical system, and an X-Y-Z table that moves only the photoelectric converter element in the X, Y and Z directions.

In the first means, the photoelectric converter element is moved along the imaging level plane of the optical system by the X-Y table, accordingly, images within the imaging size of the optical system are obtained smoothly and converted into electrical signals. In the second means, the photoelectric converter element can be moved in the X and Y and also Z directions by the X-Y-Z table, accordingly, in addition to the effect obtained by the first means, portions of the object to be inspected that are located in three-dimensional space can be brought into focus by moving the photoelectric converter element in the Z direction.

DETAILED DESCRIPTION OF THE INVENTION

Figure 1:
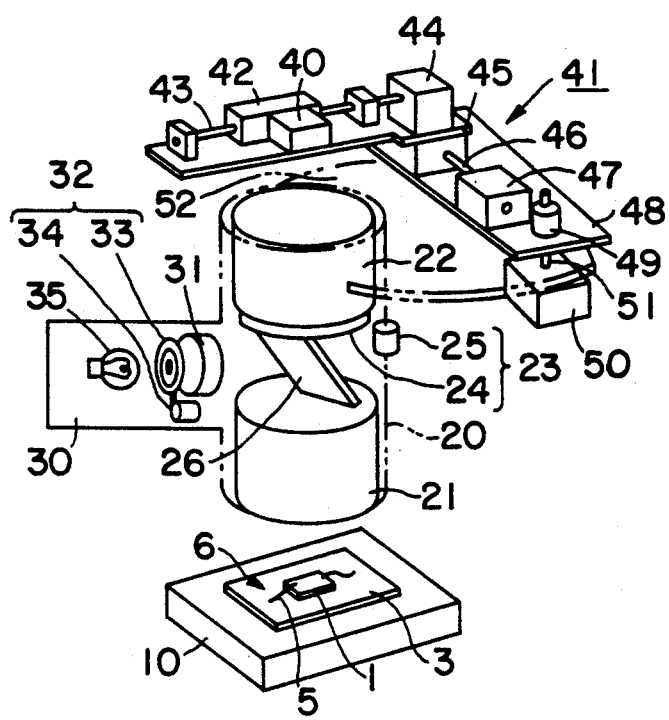
FIG. 1 illustrates the structure of the bonding wire inspection apparatus according to one embodiment of the present invention.
Figure 2:
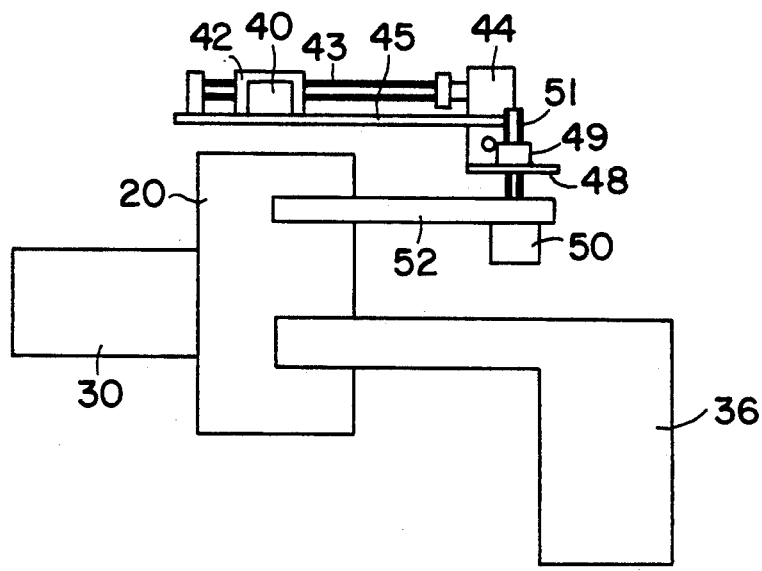
FIG. 2 is a schematic front view thereof.

One embodiment of the present invention will be described below with reference to FIGS. 1 and 2.

An optical system 20 is mounted to a mounting section 36 of an inspection apparatus so that the optical system 20 locates above the sample 6. The optical system 20 includes an objective lens group 21, an imaging lens group 22 installed above the objective lens group 21, and an electrically operated diaphragm assembly 23 that is installed beneath the imaging lens group 22. The diaphragm assembly 23 consists of a diaphragm 24, that is similar in structure to a diaphragm of an ordinary camera, and a driving section 25 that actuates the diaphragm 24.

A beam splitter 26 that is used to introduce vertical illumination from a vertical illuminator 30 and provide it vertically with the sample 6 is installed between the objective lens group 21 and the imaging lens group 22. The vertical illuminator 30 is mounted to the optical system 20 so that the illuminator 30 is next to the beam splitter 26. Inside the vertical illuminator 30, an illuminating lens 31, and an electrically operated diaphragm assembly 32 and a light source 35 are installed. The electrically operated diaphragm assembly 32 consists of, like the diaphragm assembly 23, a diaphragm 33 having a structure similar to a diaphragm of an ordinary camera and a driving section 34 that actuates the diaphragm 33.

A CCD camera 40 that converts optically imaged images into electrical signals via its photoelectric converter element 40a is installed above the imaging lens group 22. In other words, the CCD camera 40 is mounted on an X table 42 that is a part of an X-Y-Z table 41 which is movable in the X, Y and Z directions.

More specifically, a first male screw 43 which is installed in the horizontal X direction is engaged with a first female screw (not shown) provided in the X table 42. The first male screw 43 is coupled to the output shaft of an X-direction drive motor 44 that is provided on a Y table 45. A second male screw 46 is installed in the horizontal Y direction and engaged with a second female screw (not shown) provided in the Y table 45. The second male screw 46 is coupled to the output shaft of a Y-direction drive motor 47 which is mounted on a Z table 48. A third female screw 49 which is oriented in the Z (or vertical) direction is provided in the Z table 48, and a third male screw 51 coupled to the output shaft of a Z-direction drive motor 50 is engaged with the third female screw 49.

Though not shown in the Figures, the Y table 45 is supported so that it can move in the Y direction along guide rails installed on the Z table 48, and the Z table 48 is supported so that it can move in the Z direction along guide rails installed on the mounting section 36 of the inspection apparatus. In addition, the Z-direction drive motor 50 is mounted on the optical system 20 via a supporting plate 52.

The operation of the embodiment will be described with reference to FIGS. 3 and 4 and FIGS. 6 through 9.

Figure 3:
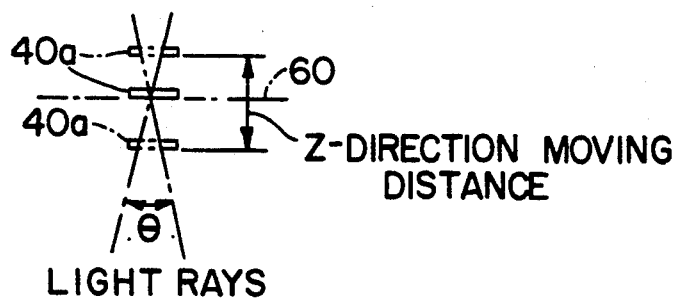
FIG. 3 illustrates the focusing of the photoelectric converter element used in the apparatus of FIG. 1.

After the sample 6 is placed on the inspection stand 10, the light source 35 of the vertical illuminator 30 is switched on. The illumination provided by the vertical illuminator 30 passes through the diaphragm assembly 32, the illuminating lens 31, the beam splitter 26 and the objective lens group 21 and then directed vertically onto the sample 6. An image of the sample 6 is taken in by the imaging lens group 22 through the objective lens group 21, the beam splitter 26 and the diaphragm assembly 23. Accordingly, focusing into the sample 6 can be accomplished by actuating the Z-direction drive motor 50 so that the Z table 48 and also the CCD camera 40 are moved in the Z-direction, resulting in that the photoelectric converter element 40a of the CCD camera 40 is caused to coincide with the imaging level 60 of the imaging lens group 22 as shown in FIG. 3. In this case, the angle theta, in FIG. 3, of the light rays 61 from the imaging lens group 22 is changed by means of the diaphragm assembly 23. Then, the CCD camera 40 is moved to position above the sample 6 by actuating the X-direction and Y-direction drive motors 44 and 47 so that the X-Y table that consists of the X table 42 and Y table 45 is moved in the X and Y directions.

In this way, images of the desired portion of the object of inspection (e.g., the shape and position of the ball 5a, the shape and position of the crescent 5b, the height of the wire 5, etc.) are obtained.

Figure 4:
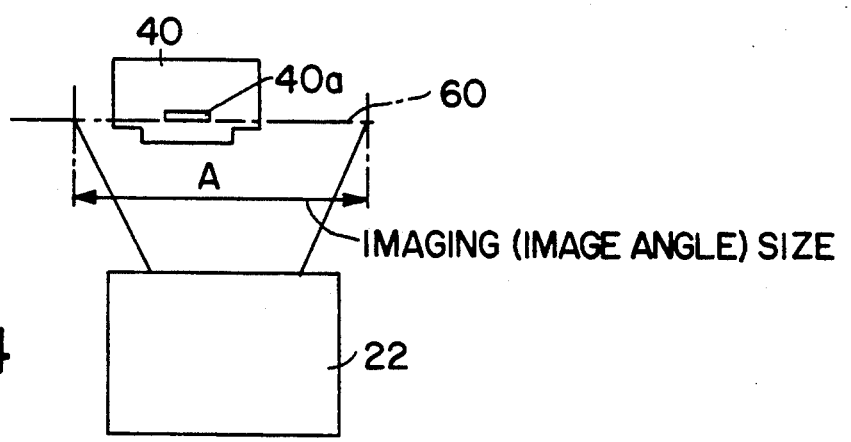
FIG. 4 illustrates the imaging level and the imaging (image angle) size of the imaging lens group of the apparatus of FIG. 1.
Figure 5:
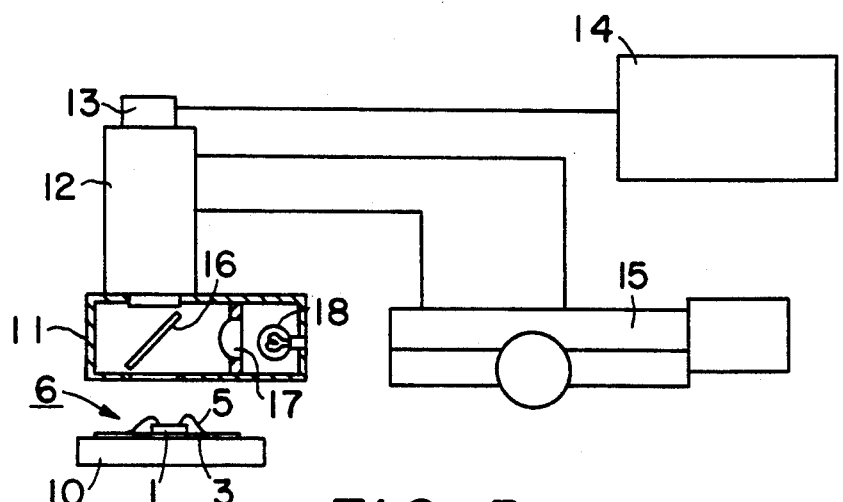
FIG. 5 illustrates the conventional bonding wire inspection apparatus.
Figure 6:
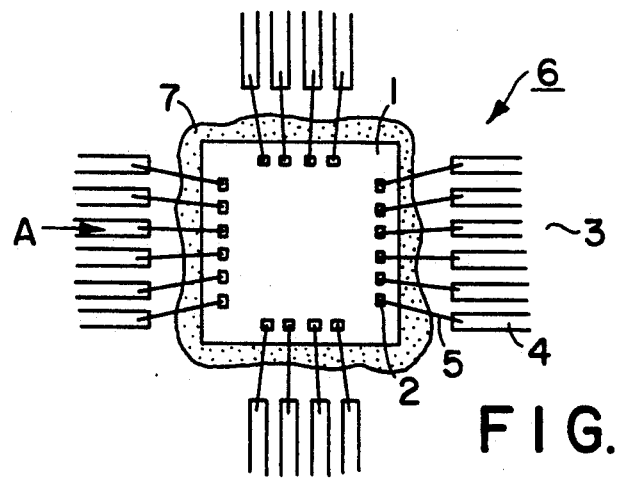
FIG. 6 is a top view of a wire-bonded semiconductor device to be inspected.
Figure 7:
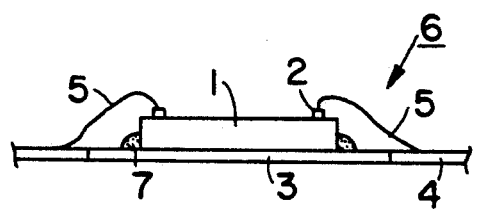
FIG. 7 is a front view thereof.
Figure 8:
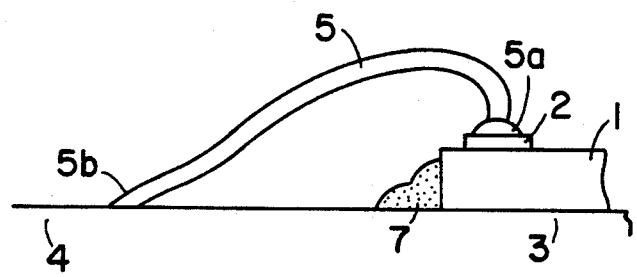
FIG. 8 is an enlarged front view thereof.
Figure 9:
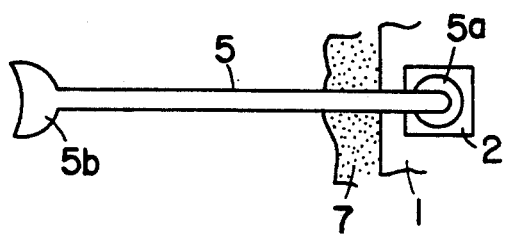
FIG. 9 is a top view thereof.

FIG. 4 shows the imaging level 60 and the imaging (image angle) size A of the imaging lens group 22.

The imaging (image angle) size that can be taken in by the photoelectric converter element 40a of the CCD camera 40 is generally 8.8 mm×6.6 mm if it is done by a ⅔ inch CCD camera. The imaging lens group 22 uses, in this embodiment, commercially marketed 35 mm square camera lenses; as a result, the imaging (image angle) size A of the imaging lens group 22 is 35 mm square. Accordingly, by moving the X table 42 and the Y table 45, it is possible to obtain desired images within the image (image angle) size A.

More specifically, by moving, via the X and Y tables 42 and 45, the photoelectric converter element 40a along the plane provided by the imaging level 60 with respect to the space imaged by the optical system 20, a same effect in terms of focusing as that which would be obtained by moving the optical system 20 or sample 6 can be obtained. Furthermore, with the use of the Z table 48 in addition to the X and Y tables 42 and 45, the photoelectric converter element 40a can be moved in Z (or vertical) direction also. Accordingly, it is possible to bring the focus of the optical system into the objects of inspection, such as the wire 5, which are in a three-dimensional space or above the pad 2.

As seen from the above, what is moved in the X and Y directions, and if necessary, in the Z direction, is the photoelectric converter element 40a which is in the CCD camera 40 and small and light weight, the X and Y tables 42 and 45 and also the Z table 48 can be made compact to move at a high speed. Furthermore, since the optical system 20 and the vertical illuminator 30 installed above the sample 6 are not moved during the focusing, the chances that dirt, etc., having a deleterious effect fall on the sample 6 are reduced greatly.

As described above in detail, the apparatus of the present invention includes an optical system that is installed above the object of inspection, an illumination means which illuminates the object to be inspected, a photoelectric converter element which is installed at the imaging level of the optical system, and an X-Y table that moves the photoelectric converter element in the X and Y directions. Furthermore, according to the apparatus of the present invention, the photoelectric converter element is movable in the Z (vertical) direction too. Accordingly, the size of the overall inspection apparatus is small, the inspection speed of the apparatus is high, and the chances that dirt, etc. falls on the sample is very small.

I claim:

1. A bonding wire inspection apparatus characterized in that said apparatus comprises: an optical system installed above an object of inspection, an illumination means which illuminates said object of inspection, a photoelectric converter element which is provided at the imaging level of said optical system, and an X-Y table which moves only said photoelectric converter element in the X and Y directions.

2. A bonding wire inspection apparatus characterized in that said apparatus comprises an optical system installed above an object of inspection, an illumination means which illuminates said object of inspection, a photoelectric converter element which is provided at the imaging level of the optical system, and an X-Y-Z table which moves only said photoelectric converter element in the X, Y and Z directions.

* * * * *